US011478166B2

(12) United States Patent
Smith

(10) Patent No.: US 11,478,166 B2
(45) Date of Patent: Oct. 25, 2022

(54) CALIBRATING A SENSING DEVICE FOR IMPROVED ANALOG-TO-DIGITAL CONVERTER RESOLUTION UTILIZATION

(71) Applicant: J. Brasch Co., LLC, Lincoln, NE (US)

(72) Inventor: Gordon Smith, Lincoln, NE (US)

(73) Assignee: J. Brasch Co., LLC, Lincoln, NE (US)

( * ) Notice: Subject to any disclaimer, the term of this patent is extended or adjusted under 35 U.S.C. 154(b) by 203 days.

(21) Appl. No.: 16/913,687

(22) Filed: Jun. 26, 2020

(65) Prior Publication Data
US 2021/0401326 A1 Dec. 30, 2021

(51) Int. Cl.
*A61B 5/11* (2006.01)
*A61B 5/00* (2006.01)

(52) U.S. Cl.
CPC ............ *A61B 5/1115* (2013.01); *A61B 5/002* (2013.01); *A61B 5/746* (2013.01); *A61B 5/0077* (2013.01)

(58) Field of Classification Search
CPC ........ A61B 5/1115; A61B 5/002; A61B 5/746
See application file for complete search history.

(56) References Cited

U.S. PATENT DOCUMENTS

| | | | |
|---|---|---|---|
| 3,770,382 A | 11/1973 | Carter et al. | |
| 5,471,208 A | 11/1995 | Sauer | |
| 10,078,952 B2 * | 9/2018 | O'Keefe, Jr. | ............ A47D 7/00 |
| 10,646,171 B2 | 5/2020 | Brasch et al. | |
| 2002/0126033 A1 | 9/2002 | Semmler et al. | |
| 2006/0014228 A1 | 1/2006 | Simpson et al. | |
| 2009/0121725 A1 | 5/2009 | Hashimoto | |
| 2013/0102061 A1 | 4/2013 | Coursey et al. | |
| 2019/0110761 A1 | 4/2019 | Brasch et al. | |
| 2019/0110763 A1 | 4/2019 | Brasch et al. | |
| 2020/0163563 A1 * | 5/2020 | Meyer | ................ A61B 5/02438 |
| 2020/0352822 A1 | 11/2020 | Marton et al. | |

FOREIGN PATENT DOCUMENTS

| | | | |
|---|---|---|---|
| CN | 103026252 A | * | 7/2011 |
| KR | 10-2001-0032491 A | | 4/2001 |
| KR | 10-2009-0048342 A | | 5/2009 |

(Continued)

OTHER PUBLICATIONS

Bilel et al., Muscle Movement Tracking Using Nanocomposite Based Pressure Sensor, 2019 16th International Multi-Conference on Systems, Signals & Devices (SSD) (pp. 483-488) 2019 (Year: 2019).*

(Continued)

*Primary Examiner* — Nabil H Syed
*Assistant Examiner* — Cal J Eustaquio
(74) *Attorney, Agent, or Firm* — Seed IP Law Group LLP

(57) ABSTRACT

Calibration of a sensing device is provided. The sensing device includes a sensor configured to sense a condition. In the sensing device, a voltage-dividing resistance and a reference voltage of an analog-to-digital converter are set to configure a quantization range of the analog-to-digital converter given characteristics of the sensor. During calibration, a binary search is performed between lower and upper limits of the voltage-dividing resistance, which is a variable resistance, to find the resistance of the voltage-dividing resistance at which the sensing device is operated.

22 Claims, 7 Drawing Sheets

(56) References Cited

FOREIGN PATENT DOCUMENTS

KR    20200005564 A  *  6/2018
KR    10-2025760 B1     9/2019

OTHER PUBLICATIONS

Lee et al., A Highly Linear, AEC-Q100 Compliant Signal Conditioning IC for Automotive Piezo-Resistive Pressure Sensors, : IEEE Transactions on Industrial Electronics (vol. 65, Issue: 9, pp. 7363-7373), 2018 (Year: 2018).*
Rahimi et al., Towards the evaluation of force-sensing resistors for in situ measurement of interface pressure during leg compression therapy, 2016 IEEE Healthcare Innovation Point-of-Care Technologies Conference (HI-POCT)(pp. 25-28); 2016 (Year: 2016).*
U.S. Appl. No. 16/159,412, filed Oct. 12, 2018, Assistive Technology for Operating Nursing Homes and Other Health Care Facilities.
U.S. Appl. No. 16/159,478, filed Oct. 12, 2018, Assistive Technology for Operating Nursing Homes and Other Health Care Facilities.
International Search Report, dated Sep. 28, 2021, for International Application No. PCT/US2021/036929, 4 pages.

* cited by examiner

CALIBRATING A SENSING DEVICE FOR IMPROVED ANALOG-TO-DIGITAL CONVERTER RESOLUTION UTILIZATION

BACKGROUND

Sensing devices include sensors that sense a condition, such as pressure, luminance or light intensity, temperature, among others. Variations during sensor production, process or manufacturing, can result in variable response characteristics of sensors. As a result, two pressure sensors that are presumed to be identical and have the same part number and associated specification sheet may have different pressure response characteristics.

DETAILED DESCRIPTION

The inventors recognized that when two sensors (having different characteristics) are used in identically-configured pressure sensing devices, the capability and resolution of the pressure sensing devices are not fully exploited. For example, pressure sensing devices include analog-to-digital converters (ADCs) that digitize voltage. When the ADCs are similarly or identically-configured and used with sensors having different characteristics, various ranges of the span of the ADCs become unutilized during operation. This results in a loss of ADC resolution. Additionally, voltages corresponding to some pressure measurements may fall outside the range of the ADCs.

Described herein is a sensing device that is calibrated to improve the interoperability between an ADC and a sensor of a sensing device and better use the resolution of the ADC. The sensing device is calibrated in a calibration stage. In an embodiment, the calibration includes setting a reference voltage of the ADC and a resistance value of a voltage-dividing resistance. The sensing device then operates with the reference voltage and the resistance value that are set during the calibration stage.

Figure 1:
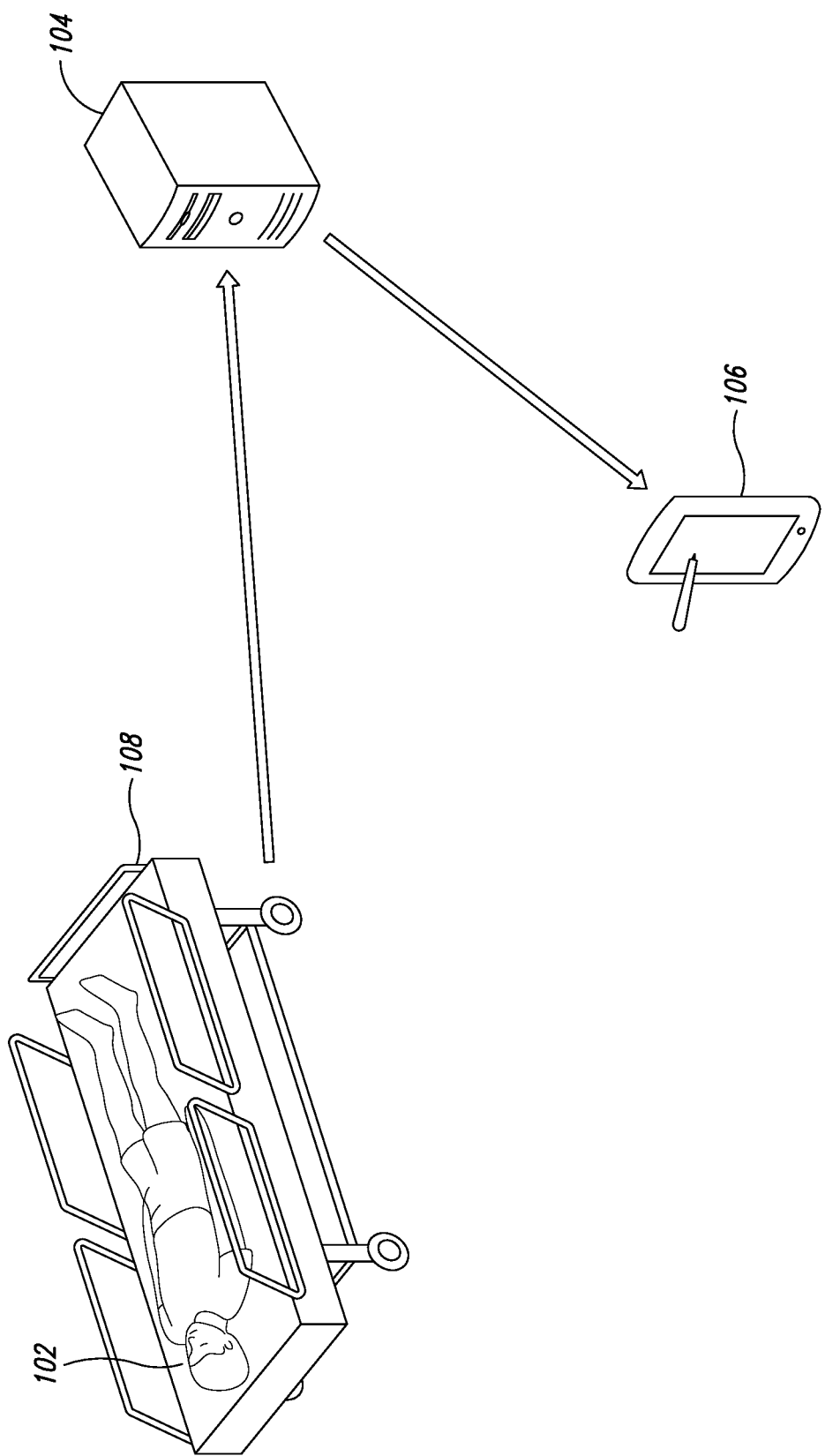
FIG. 1 is an environmental diagram showing a system for measuring and reporting pressure applied to a pressure sensing device.

FIG. 1 shows a system 100 for measuring and reporting pressure applied to a pressure sensing device 102. The system 100 includes the pressure sensing device 102, a server 104 and a user device 106. The pressure sensing device 102 is illustrated in FIG. 1 as a pressure sensing pad positioned on a care facility bed 108 but, in various embodiments, may be any type of sensor. The pressure sensing device 102 measures pressure applied thereto and outputs data representative of the pressure. Although the term pressure is used herein, it is understood that the pressure sensing device 102 may measure or detect any applied force or impact.

In some embodiments, the pressure sensing device 102 is used in a care facility, such as a nursing home or a hospital, among others. The pressure sensing device 102 detects whether a person under care was dislodged or removed from the care facility bed 108. In the event of a fall, the pressure sensing device 102 is operative to detect the fall by virtue of a removal applied pressure. For example, the pressure sensing device 102, as a pressure sensing pad, may be positioned below, within, below or over a bedding, mattress or cushion of the care facility bed 108. The pressure sensing device 102 detects the pressure applied by the person under care. The detected pressure is used to determine whether a person is positioned on the care facility bed 108, whereby a relatively small pressure measurement indicates that the person under care is no longer positioned on the care facility bed 108. It is noted that although a care facility bed 108 is shown in FIG. 1, the pressure sensing device 102 may be used in a wheelchair, field stretcher, chair, couch, crib, cradle or cot, among others. The pressure sensing device 102 sends the data representative of the pressure to the server 104.

In some embodiments, the server 104 is any type of centralized or distributed computer system configured to execute instructions stored in memory (not shown). The server 104 includes a processor, microprocessor, controller or microcontroller, among others, having an arithmetic and logic unit (ALU), central processing unit (CPU) or graphics processing unit (GPU), among other computational units. When the executable instructions are executed by the server 104, the executable instructions cause the server 104 to perform the functions or techniques described herein.

The server 104 includes a communication device. In some embodiments, the communication device is a modem or transceiver, among others. The server 104 receives the data representative of the pressure from the pressure sensing device 102. The server 104 stores the data and/or send the data to the user device 106. Further, the server 104 evaluates the data to determine whether the person is (or is not) positioned on the care facility bed 108 and send data representative of whether the person is positioned on the care facility bed 108 to the user device 106.

In some embodiments, the user device 106 is any type of computer system, such as a consumer electronics device including a tablet, computer or smartphone, among others. In some embodiments, the user device 106 is operated or used by a user who may be a care professional caring for the person under care. The user device 106 receives the data representative of whether the person is positioned on the care facility bed 108. In response to the data indicating that the person is not positioned on the care facility bed 108, the user device 106 outputs a notification to the user indicating that the person is not or no longer positioned on the care facility bed 108, for example, by displaying an alert on a display of the user device 106. The alert triggers the care professional to visit, check on or examine the person under care.

It is noted that in various embodiments, the pressure sensing device 102 alternatively, or in addition to sending the data representative of the pressure to the server 104, sends the data representative of the pressure directly to the user device 106. The user device 106 evaluates the data to determine whether the person is positioned on the care facility bed 108. In response to determining that the person is not positioned on the care facility bed 108, the user device 106 outputs the notification to the user.

Figure 2:
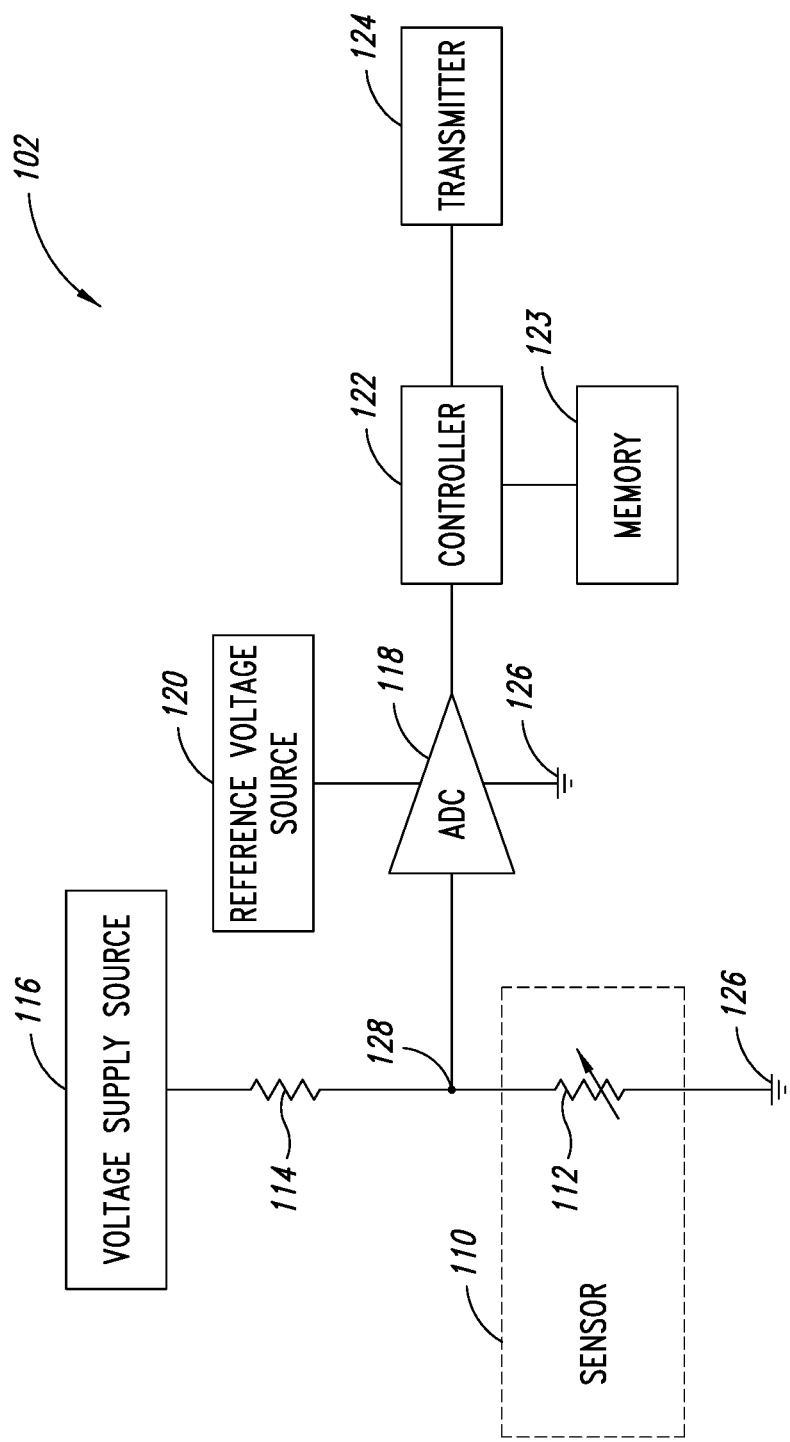
FIG. 2 is a modified circuit diagram showing the pressure sensing device.

FIG. 2 shows a diagram of the pressure sensing device 102. The pressure sensing device 102 includes a sensor 110 having a variable resistance 112, a voltage-dividing resistance 114, a voltage supply source 116, an analog-to-digital converter (ADC) 118, a reference voltage source 120, a controller 122, memory 123 and a transmitter 124.

The sensor 110 is a pressure sensor that is configured to sense pressure (or impact or force) and vary the variable resistance 112 based to the sensed pressure. In some embodiments, the relationship between the sensed pressure and the resistance of the variable resistance 112 is linear or non-linear, positively or negatively correlated and/or proportional or inversely proportional. The sensor 110 exhibits its output of sensed pressure as the variable resistance 112. The variable resistance 112 is serially coupled to the voltage-dividing resistance 114 in a voltage divider configuration.

The variable resistance 112 has a first terminal coupled to a ground node 126, which provides a ground or another reference voltage or a path thereto. The variable resistance 112 has a second terminal coupled to a tap node 128.

The voltage-dividing resistance 114 is a variable resistance that is set to a particular resistance value based on a calibration performed on the pressure sensing device 102 as described herein. After calibration, e.g., during operation of the pressure sensing device 102, the voltage-dividing resistance 114 has a resistance level with which it is calibrated or configured.

In various embodiments, the voltage-dividing resistance 114 is of a variety of types of controllable and changeable resistance. In some embodiments, the voltage-dividing resistance 114 is electrically-controllable, whereby the voltage-dividing resistance 114 has a control terminal configured to receive data representative of the resistance to be provided by the voltage-dividing resistance 114. In response to receiving the data representative of the resistance, the voltage-dividing resistance 114 provides the resistance across its electrically-conductive terminals. In some embodiments, the voltage-dividing resistance 114 is a digital resistor, switched-capacitor resistor, potentiometer or rheostat, among others.

The voltage-dividing resistance 114 has a first terminal coupled to the tap node 128 and a second terminal coupled to the voltage supply source 116. The voltage supply source 116 is any type of voltage source configured to provide a supply voltage. In some embodiments, the voltage supply source 116 is a node coupled to a voltage source, e.g., of the pressure sensing device 102. In some embodiments, the voltage supply source 116 supplies a rail voltage (or system voltage ($V_{dd}$)) having a constant or substantially constant level. In some embodiments, the reference voltage of the ADC 116 is lower than the system voltage ($V_{dd}$) of the pressure sensing device 102. In some embodiments, the voltage supply source 116 is coupled to a regulator or a converter, among others, of the pressure sensing device 102.

The ADC 118 has an input coupled to the tap node 128 and an output. The ADC 118 has a first reference voltage input coupled to a ground node 126 and a second reference voltage input coupled to the reference voltage source 120. The ADC 118 is any type of device configured to convert an analog voltage supplied at the input to a digital voltage supplied at the output. In some embodiments, the ADC 118 supplies a read out of the analog voltage, where the read out is a digital signal representative of the analog voltage. The ADC 118 has a resolution that dictates the number quantization levels of the ADC 118. For example, a resolution of 8 or 10 bits results in 256 or 1024 quantization levels, respectively. In some embodiments, the ADC 118 outputs the digital signal representative of the analog voltage serially or in parallel in which case the output of the ADC 118 is an output bus. The output bus includes lines that each correspond to one bit of the resolution of the ADC 118. For example, an 8-bit ADC has an output bus of at least eight lines.

The reference voltage source 120 supplies a DC voltage of a configurable or controllable level. In some embodiments, the reference voltage source 120 is a regulator or a converter, among others. In some embodiments, the reference voltage source 120 is a node supplied by the regulator or converter, among others. In some embodiments, reference voltage source 120 is a DC-DC regulator or is supplied by the DC-DC regulator. In some embodiments, the reference voltage source 120 is configured to supply a constant or substantially constant voltage level during operation of the pressure sensing device 102. In some embodiments, during calibration of the pressure sensing device 102, the reference voltage source 120 is controlled to supply a voltage level that is changed during calibration as described herein.

The controller 122 has an input coupled to the output of the ADC 118 and an output. The controller 122 is also operatively coupled to the memory 123. In some embodiments, the controller 122 is any type of circuit or device configured to execute instructions (computer-executable instructions) that, when executed by the controller, cause the controller 122 to operate as described herein. In some embodiments, the controller 122 is a processor or a microcontroller and includes a central processing unit (CPU) or any other type of processing unit. The memory 123 may be any type of non-transitory computer-readable storage medium. In some embodiments, the memory 123 is read-only memory (ROM) or random access memory (RAM), among others. In some embodiments, the memory 123 is static or dynamic. The memory 123 stores the computer-executable instructions that are retrieved or accessed by the controller 122 for execution. The computer-executable instructions, when executed by the controller 122, cause the controller 122 to operate as described herein.

The transmitter 124 has an input coupled to the output of the controller 122. The transmitter 124 is any type of communication device configured to transmit data. In some embodiments, the transmitter 124 is a transceiver or modem, among others. In some embodiments, the transmitter 124 is configured to communicate using any type of communication protocol. In some embodiments, the protocol is a cellular communication protocol, such as long term evolution (LTE), or a wireless communication protocol, such as the Institute of Electrical and Electronics Engineers (IEEE) 802 protocol (colloquially known as "Wifi"), among others. In some embodiments, the communication protocol is Bluetooth®.

During operation, the sensor 110 senses pressure and sets the resistance of (or presents a resistance on) the variable resistance 112 in accordance with the sensed pressure. The supply voltage is divided by the voltage divider including the dividing resistance 114 and the variable resistance 112. A voltage of the tap node 128 is a product of the supply voltage by a ratio of the variable resistance 112 to the sum of the variable resistance 112 and the dividing resistance 114. The voltage divider converts the variable resistance 112 into a voltage at the tap node 128. The ADC 118 taps the voltage divider at the tap node 128. The ADC 118 converts the voltage of the tap node 128, which is analog, into digital format. The ADC 118 may be said to discretize the voltage of the tap node 128 and, thus, the sensed pressure.

The controller 122 receives the converted voltage and determines the sensed pressure based on the converted voltage. In some embodiments, a relationship between sensed pressure and the resistance of the variable resistance 112 is known a priori. In some embodiments, the resistance of the dividing resistance 114 and the supply voltage are also known a priori. Thus, the controller 122 determines the resistance of the variable resistance 112 from the converted voltage and determine the sensed pressure from the resistance of the variable resistance 112.

The controller 122 outputs the sensed pressure to the transmitter 124. The transmitter 124 transmits the sensed pressure to the server 104 or directly to the user device 106 as described herein. The controller 122 outputs the sensed pressure to the transmitter 124. The pressure sensing device 102, server 104 or user device 106 compares the pressure to a threshold value indicative of whether the person under care is applying pressure to the pressure sensing device 102. In some embodiments, in an event that the pressure is below the threshold, the alert is provided indicating that the person is not positioned on the sensor 110. Reference herein is made to U.S. Provisional Patent Application No. 62/572,373 filed on Oct. 13, 2017, U.S. patent application Ser. No. 16/159,412 filed Oct. 12, 2018, U.S. Provisional Patent Application No. 62/580,928 filed on Nov. 2, 2017, U.S. patent application Ser. No. 16/159,439 filed on Oct. 12, 2018, U.S. Provisional Patent Application No. 62/572,379 filed on Oct. 13, 2017, U.S. patent application Ser. No. 16/159,478 filed on Oct. 12, 2018, U.S. Provisional Patent Application No. 62/643,695 filed on Mar. 15, 2018 and U.S. Provisional Patent Application No. 62/691,960 filed on Jun. 29, 2018, which are incorporated by reference herein and disclose use and processing of the measured pressure. Where a document incorporated by reference and the present application conflict, the present application controls.

It is noted that due to various factors, the resistive response to pressure of various sensors are different. For example, manufacturing or process variations results in different sensors having different resistive responses to pressure. Due to the variation, a single configuration of the pressure sensing device 102 does not result in optimal use of different sensors to detect pressure. Accordingly, at manufacturing/assembly, installation or relocation, the pressure sensing device 102 is configured in a calibration stage. The calibration improves the precision of the pressure sensing device 102 and better tailors other elements of the pressure sensing device 102 to specific or unique characteristics of the sensor 110.

Figure 3:
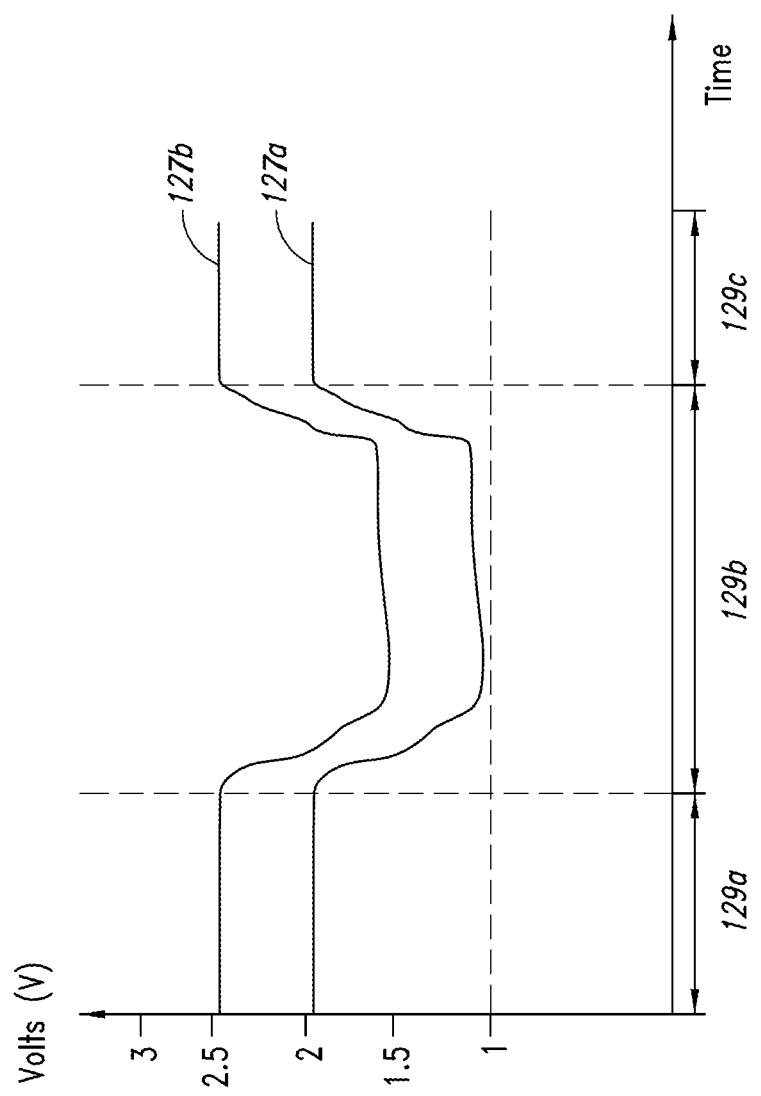
FIG. 3 is a timing diagram showing an example of voltage responses observed at a tap node of the pressure sensing device for two sensors.

FIG. 3 shows an example of voltage responses 127a, 127b observed at the tap node 128 of the pressure sensing device 102 for two sensors 128a, 128b. A first voltage response 127a is observed at the tap node 128 of the pressure sensing device 102 when a first sensor 128a is used in the pressure sensing device 102. A second voltage response 127b is observed at the tap node 128 of the pressure sensing device 102 when a second sensor 128b is used in place of the first sensor 128a in the pressure sensing device 102.

During a first time interval 129a, pressure is not applied to the sensors 128a, 128b. Due to the inverse relationship of the variable resistance 112 with pressure, the variable resistance 112 increases to substantially an upper limit of the variable resistance 112. Consequently, the voltage responses 127a, 127b are each maximized. During a second time interval 129b, pressure is applied to the sensors 128a, 128b. The variable resistance 112 decreases in relation to pressure. Consequently, the voltage responses 127a, 127b also decrease. During a third time interval 129c, pressure is removed from the sensors 128a, 128b. The variable resistance 112 increases resulting in substantially maximized voltage responses 127a, 127b. Due to the different responses of the first and second sensors 128a, 128b, the resolution and quantization levels of the ADC 118 are steered to different voltage ranges for each sensor to improve ADC 118 resolution utilization.

In some embodiments, configuring pressure sensing devices includes setting a resistance of the dividing resistance 114 and the reference voltage of the ADC 118 to values that focus the span of the ADC 118 on operational ranges of the sensors or variable resistances 112 thereof. The span of the ADC 118 is a range between the voltages provided to the reference voltage inputs of the ADC 118 (e.g., between ground and the reference voltage). For example, due to the fact that the first sensor 128a does not utilize the voltage range above 2 volts (V), a pressure sensing device 102 using the first sensor 128a is configured to cap the span of the ADC 118 at 2V. Further, because the second sensor 128b utilizes the voltage range between 2 and 2.5V, a pressure sensing device 102 using the second sensor 128b is configured to cap the setting at the range of the ADC 118, e.g., at 2.5V or above including 2.6 or 2.7V.

Configuring the pressure sensing devices reduces quantization noise of the ADC 118. Quantization noise is proportional to a difference between an analog input voltage and the corresponding converted voltage (digitized voltage). To better use the span of the ADC 118 and to minimize quantization noise, it is desirable to optimally set the dividing resistance 114 and the reference voltage provided to the ADC 118 by the reference voltage source 120.

Figure 4:
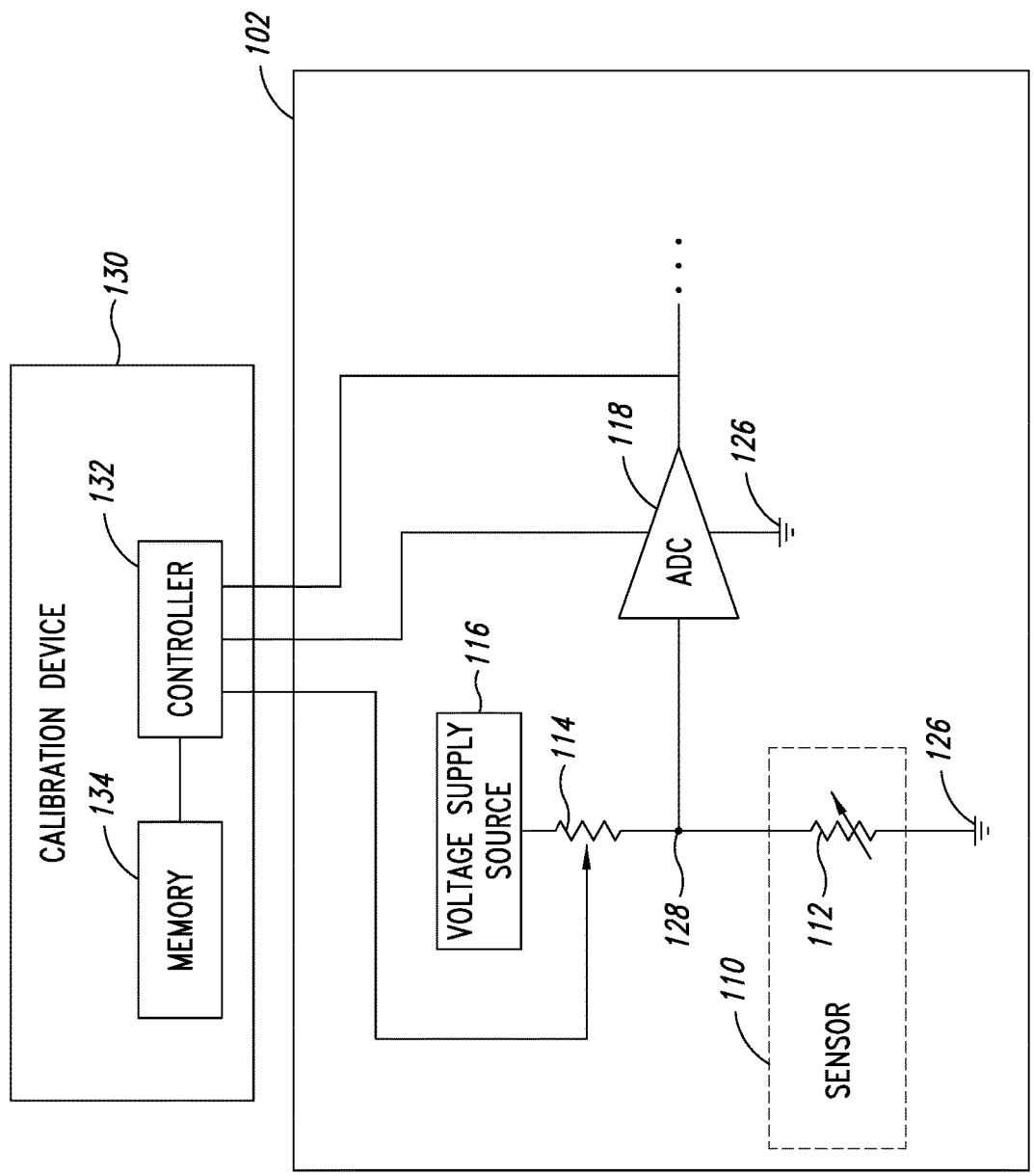
FIG. 4 is a modified circuit diagram showing a calibration device coupled to the pressure sensing device.

FIG. 4 shows a calibration device 130 coupled to the pressure sensing device 102. The calibration device 130 calibrates the pressure sensing device 102. In some embodiments, the calibration device 130 is removably coupled to the pressure sensing device 102 during a calibration stage and decoupled from the pressure sensing device 102 after completion of the calibration stage, whereby the pressure sensing device 102 operates independently. In some embodiments, the calibration device 130 is permanently coupled to the pressure sensing device 102.

The calibration device 130 includes a controller 132 and memory 136. In some embodiments, the calibration device 130 includes other elements than those shown in FIG. 4. In some embodiments, the controller 132 is any type of device or circuit that is configured to execute instructions (computer-executable instructions) that, when executed by the controller 132, cause the controller 132 to operate as described herein. For example, in some embodiments, the controller 132 is a processor or a microcontroller and includes a central processing unit (CPU) or any other type of processing unit.

The memory 136 is any type of non-transitory computer-readable storage medium. In some embodiments, the memory 136 is read-only memory (ROM) or random access memory (RAM), among others. Further, in some embodiments, the memory 136 is static or dynamic. The memory 136 stores the computer-executable instructions that are retrieved or accessed by the controller 132 for execution. The computer-executable instructions, when executed by the controller 132, cause the controller 132 to operate as described herein including calibrating the pressure sensing device 102.

The controller 132 and memory 136 are operatively coupled. The controller 132 has a first output coupled to a control input of the voltage-dividing resistance 114, which as a controllable and variable resistance is shown in FIG. 4 to have the control input. The controller 132 commands, via the first output, the voltage-dividing resistance 114 to present or provide a specific resistance value. The controller 132 has a second output coupled to the second reference voltage input of the ADC 118. The controller 132 supplies, via the second output, a reference voltage having a specific level to the ADC 118. During calibration, the reference voltage is yet to be determined and accordingly the reference voltage source 120 is yet to be coupled to the second reference voltage input as would be during operation and as shown in FIG. 2. The controller 132 has an input coupled to the output of the ADC 118. The controller 132 receives, via the input, the converted voltage output of the ADC 118.

Figure 5:
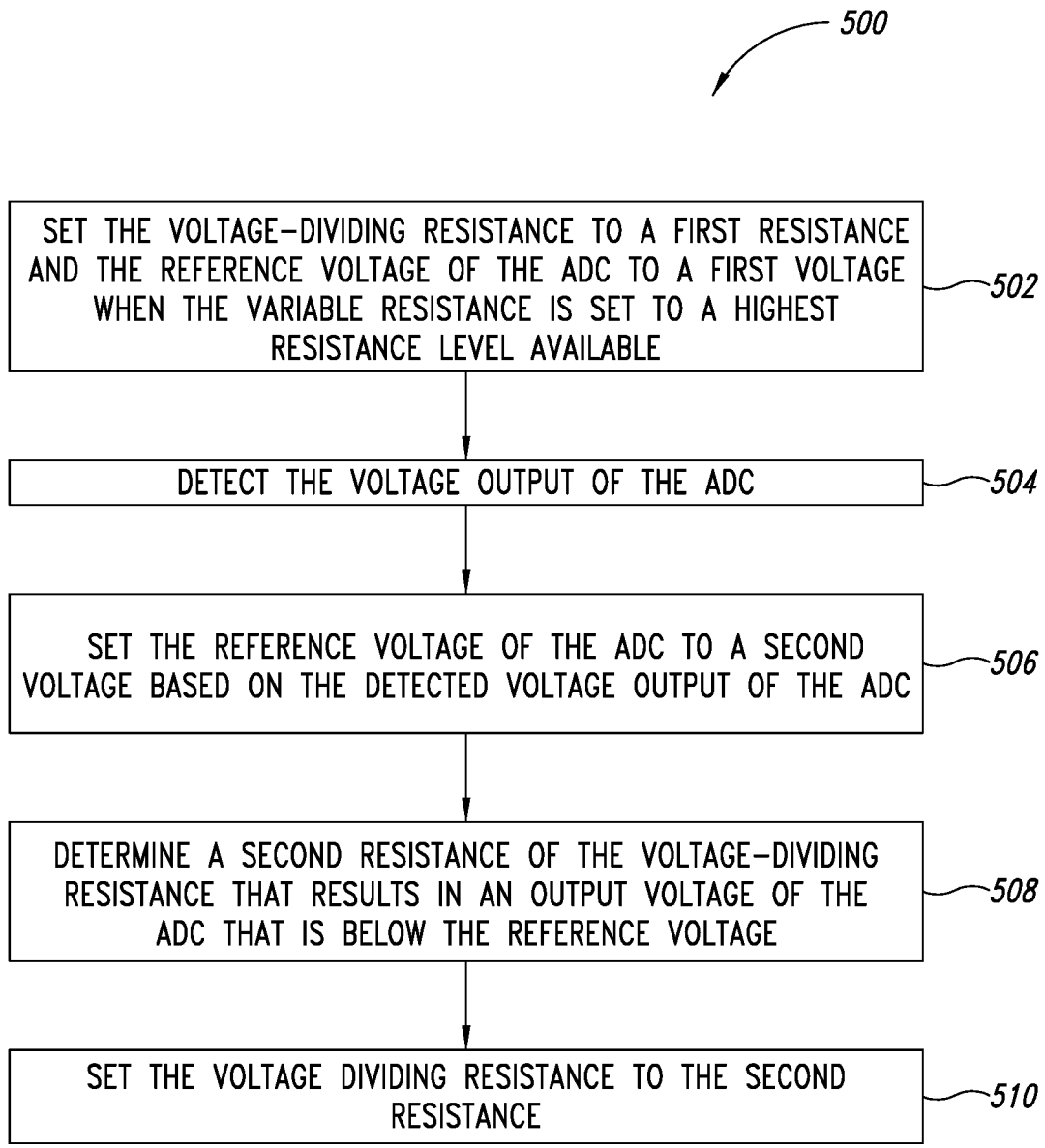
FIG. 5 is a flow diagram showing a method for calibrating the pressure sensing device.

FIG. 5 shows a method 500 for calibrating the pressure sensing device 102. In the method 500, at 502, the calibration device 130 (or controller 132 thereof) sets the voltage-dividing resistance 114 to a first resistance and the reference voltage of the ADC 118 to a first voltage when the variable resistance 112 is set to a highest resistance level available. In some embodiments, the first resistance is a lowest resistance level of the voltage-dividing resistance 114 that is available or higher than the lowest resistance level. In some embodiments, the first voltage is a highest voltage level supported by the ADC 118.

The calibration device 130 commands the voltage-dividing resistance 114 to operate and provide the first resistance. In some embodiments, the first resistance is close to zero ohms ($\Omega$). The calibration device 130 outputs to the ADC 118 the first voltage. For example, if the range of the ADC 118 is 0 to 10 volts (V), the calibration device 130 outputs the reference voltage having a level of 10V.

As described herein, the variable resistance 112 has the highest resistance level available when pressure is not applied to the sensor 110. In some embodiments, in the event of the pressure sensing device 102 is a mat or pad, it is ensured that pressure is removed by refraining from placing a body on the mat or pad. It is noted that although, pressure is described herein to facilitate description, in the event that the sensor 110 senses a condition or metric other than pressure, the condition or metric (or stimuli or catalyst thereof) is removed. In some embodiments, the sensor 100 senses temperature, visible, infrared or ultraviolet light or intensity, or humidity, among others. In some embodiments, the variable resistance 112 is inversely proportional to pressure and, accordingly, removing or refraining from applying pressure results in maximizing the variable resistance 112 presented by the sensor 110.

When the voltage-dividing resistance 114 is at the first resistance (e.g., lowest resistance level available) and the variable resistance 112 is at the highest resistance level available, a maximum voltage of the tap node 128 (and of the output of the ADC 118) that is reached during operation is identified.

While the set conditions are in effect, the calibration device 130 detects the output voltage of the ADC 118 at 504. The detected output voltage is the maximum output voltage for the pressure sensing device 102 and sensor 110 thereof. At 506, the calibration device 130 sets the reference voltage of the ADC 118 to a second voltage based on the detected output voltage of the ADC 118. In some embodiments, the second voltage is a voltage level below the detected output voltage of the ADC 118. For example, the reference voltage of the ADC 118 is set to a voltage level that is 0.1, 0.5 or 1V below the detected output voltage of the ADC 118.

At 508, the calibration device 130 determines a second resistance of the voltage-dividing resistance 114 that results in an output voltage of the ADC 118 that is below the reference voltage. In some embodiments, the calibration device 130 determines the second resistance of the voltage-dividing resistance 114 computationally, empirically and/or iteratively. In some embodiments, the calibration device 130 determines the second resistance of the voltage-dividing resistance 114 in a deterministic manner.

The closer the output voltage is to the reference voltage (while being less than the reference voltage), the better the utilization of the quantization levels of the ADC 118 and sensor 110 thereof under calibration. Thus, it is desirable to determine the second resistance that results in bridging a gap between the output voltage and the reference voltage, while retaining the output voltage at a level less than that of the reference voltage. Retaining the output voltage at a level less than the reference voltage avoids ADC 118 clipping. For example, for an 8-bit ADC with 256 quantization levels ranging from 0 to 255, the second resistance that results in the ADC output being at the 254th, 253rd or 250th quantization level, among others, is determined. In some embodiments, the 255th quantization level corresponds to the reference voltage or a clipped voltage that is greater than the reference voltage. A binary search is described herein to determine the second resistance iteratively. As the number of iterations of the binary search increases, so does the likelihood of an output level closer to the reference voltage.

At 510, the calibration device 130 sets the voltage-dividing resistance 114 to the determined second resistance. The pressure sensing device 102 is operated with the reference voltage of the ADC 118 as set at 506 and the voltage-dividing resistance 114 as set at 510.

To determine the second resistance that results in an output voltage of the ADC 118 that is below the reference voltage, the calibration device 130 performs a binary search for the second resistance. The voltage-dividing resistance 114, as a variable resistance, has known minimum and maximum available resistance levels. The voltage-dividing resistance 114 is initially set to the first resistance. In some embodiments, the first resistance corresponds to the minimum available resistance level. The calibration device 130 performs the binary search to determine the second resistance that results in the output voltage of the ADC 118 being below the reference voltage.

In some embodiments, the voltage supply source 116 supplies the system voltage ($V_{dd}$) of the pressure sensing device 102 (e.g., 3.3V) to the voltage-dividing resistance 114. Thus, the voltage divider (including the voltage-dividing resistance 114 and the variable resistance 112) is coupled between ground voltage (e.g., 0V) and the system voltage ($V_{dd}$) (e.g., 3.3V). This allows the voltage divider to vary the sensor 110 reading in a range of 3.3V and 0V asymptotically. The reference voltage of the ADC 116 is lower than the system voltage ($V_{dd}$) and within the range. Thus, the calibration device 130 determines a specific matching resistance of the voltage-dividing resistance 114. The matching resistance places the maximum reading of the sensor 110 (or zero pressure point) at the reference voltage of the ADC 118. This maximizes the available ADC range as it relates to the sensor 110 output and provides the maximum amount of sensor 110 sensitivity. In some embodiments, precise calibration is accomplished even when only a small or moderate difference, e.g., due to manufacturing or materials, causes each sensor's 110 resistance 112 to vary.

Conversely, the ability to calibrate may not be available if the reference voltage of the ADC 118 was equal to the system voltage. That is due to the fact that no amount of voltage-dividing resistance 114 adjustment could be made to precisely calibrate the pressure sensing device 102 to a specific sensor.

Figure 6:
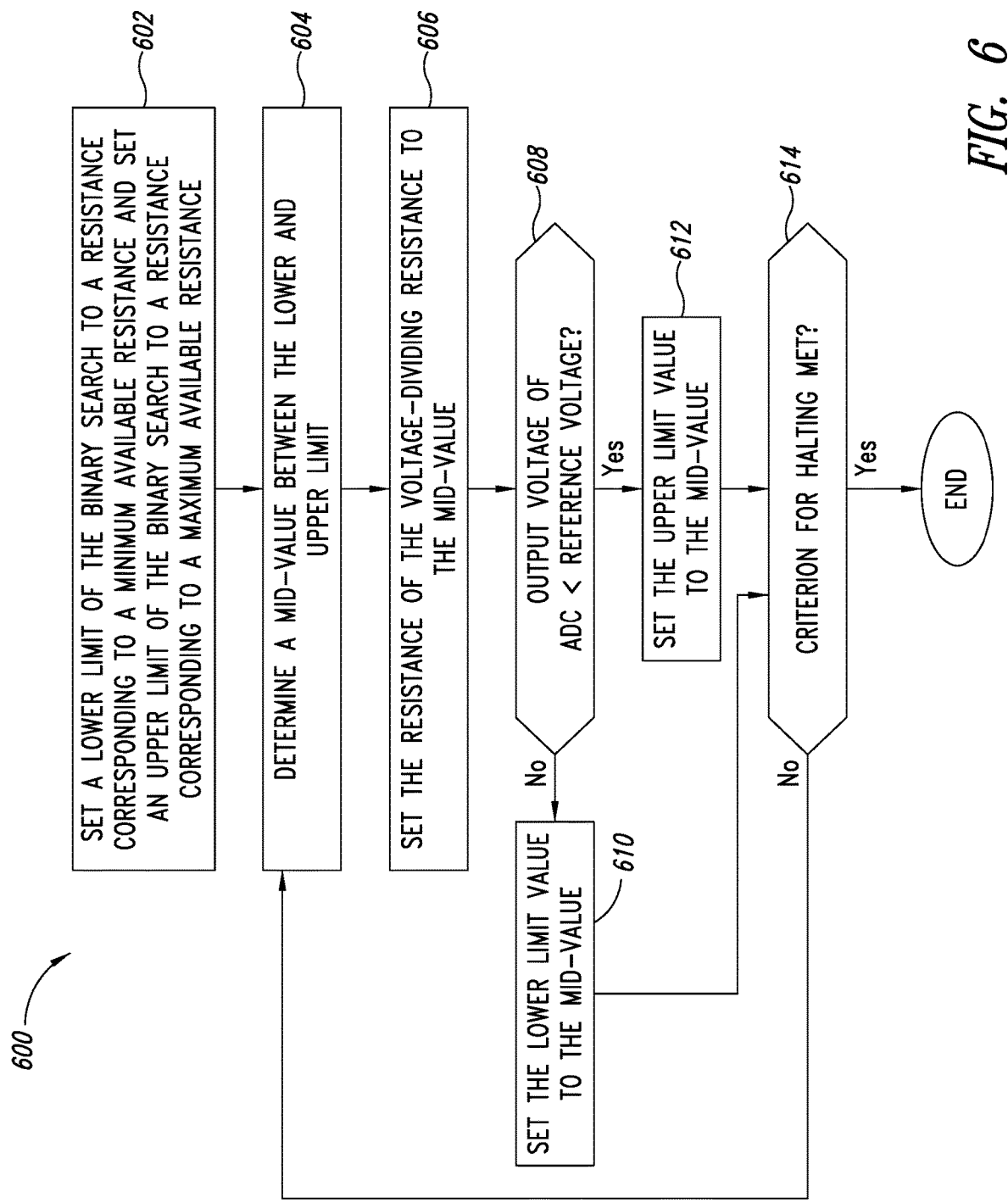
FIG. 6 is a flow diagram showing a method for performing the binary search to determine a resistance level of the voltage-dividing resistance.

FIG. 6 shows a flow diagram of a method 600 for performing the binary search to determine the second resistance of the voltage-dividing resistance 114. In the method 600, the calibration device 130 (or the controller 132 thereof), at 602, sets a lower limit of the binary search to a resistance corresponding to the minimum available resistance and sets an upper limit of the binary search to a resistance corresponding to the maximum available resistance. In some embodiments, the lower limit is set to the minimum available resistance or a resistance higher than the minimum. Similarly, the upper limit is set to the maximum available resistance or a resistance lower than the maximum.

The limits of the binary search are bookended by the minimum and maximum available resistances of the voltage-dividing resistance 114. At 604, the calibration device 130 determines a mid-value between the lower limit and the upper limit. In some embodiments, the mid-value is any value between the lower and upper limits. In some embodiments, the mid-value is a mean of the lower and upper limits or any other function of the lower and upper limits.

The calibration device 130 tests the mid-value to determine whether the mid-value satisfies the sought condition of the output voltage of the ADC 118 being below the reference voltage and to guide the direction of the binary search. The calibration device 130 sets the resistance of the voltage-dividing resistance 114 to the mid-value at 606 and determines whether the output voltage of the ADC 118 is less than the reference voltage at 608.

If a negative determination is made, it is concluded that the mid-value is lower than desired and does not result in the condition being met. In this case, a resistance that is higher than the mid-value is tested. Accordingly, if a negative determination is made, the calibration device 130, at 610, sets the lower limit to the mid-value. Accordingly, the calibration device 130 establishes the mid-value as the lower limit of the binary search, whereas the upper limit of the binary search remains at the resistance corresponding to the maximum available resistance and satisfies the sought condition. The method 600 then proceeds to 614, where the calibration device 130 determines whether a criterion for halting met. If a negative determination is made at 614, the method proceeds to 604, where a subsequent mid-value is determined based on the upper limit and newly-established lower limit. The subsequent mid-value is tested and used to guide the direction of the binary search again.

If a positive determination is made, it is concluded that the mid-value satisfies the sought condition. The binary search is continued to determine a lower value than the mid-value that also satisfies the condition. To do so, the calibration device 130 sets the upper limit of the binary search to the mid-value at 612. Thus, the binary search is narrowed and the determination at 608 steers the direction of the binary search to lower resistances. In some embodiments, as a result of each iteration, the binary search range between the lower and upper limits is halved.

The calibration device 130 at any point ends the method 600 and utilizes a resistance that meets the established condition. In some embodiments, halting the binary search is based on any criterion, such as the difference between the output voltage of the ADC 118 and the reference voltage or the number of iterations of the binary search that have been performed, whereby an iteration is the number of times that the output voltage of the ADC 118 was compared to the reference voltage or the number of times that the comparison yielded a positive determination. In some embodiments, the criterion is a duration of time consumed in performing the binary search. For example, the duration of time may be limited to five seconds and upon reaching the time limit, the method 600 is halted.

At 614, the calibration device 130 determines whether a criterion for halting met. In some embodiments, the criterion for halting is met when the difference between the output voltage of the ADC 118 and the reference voltage is below a threshold, such as 0.1 or 0.01V. In some embodiments, the criterion for halting is met when the number of iterations of the binary search that have been performed exceeding a threshold, such as 10 or 50 iterations, where an iteration is the number of times that the output voltage of the ADC 118 was compared to the reference voltage or the number of times that the comparison yielded a positive determination. In some embodiments, the criterion for halting is met when the duration of time consumed in performing the binary search reaches a threshold, such as five or ten seconds. In some embodiments, the criterion for halting is met when the binary search has fully converged on the resistance of the voltage-dividing resistance. In some embodiments, the binary search fully converges when the determination, at 604, does not result in a new or different mid-value or when setting the resistance, at 604, does not result in a new or different resistance. In some embodiments, a complex criterion for halting is used. The complex criterion is based on multiple criteria for halting, such as two or more of the criteria for halting described herein.

In some embodiments, if a positive determination is made, a last-determined resistance that meets the sough condition is used as the second resistance. Conversely, if a negative determination is made, the method 600 proceeds to 604 at which the calibration device 130 determines a mid-value between the lower and upper limits.

In some embodiments, the pressure sensing device 102 is a pad and a plurality of pads that are used in a particular facility are calibrated. A patient is moved between two or more pads due to patient relocation, pad replacement or pad failure, among other reasons. As a result of the calibration, data collected from the different pads more closely match each other despite manufacturing variation. Data collected before and after the patient is moved is available for combining or comparison and is treated as if the data is collected by the same pad. In some embodiments, the data from multiple of the pads is used to train a machine learning model, among others.

In an embodiment, the voltage-dividing resistance 114 is two or more variable resistances coupled in series. The two or more variable resistances are adjustable by the controller 132 of the calibration device 130. Use of two or more variable resistances allows for finer granularity in selecting and testing resistance values.

In an embodiment, the calibration of the pressure sensing device 102 described herein is performed by the controller 122. For example, instead of utilizing an independent calibration device 130 to calibrate the pressure sensing device 102, the controller 122 is configured to self-calibrate the pressure sensing device 102 using the techniques described herein.

It is noted that the embodiments described herein are applicable to other configurations of the pressure sensing device 102. For example, if the variable resistance 112 is proportional to pressure, the positioning of the variable resistance 112 and the voltage-dividing resistance 114 in the voltage divider is swapped. Further, a reference voltage provided to the first reference voltage input of the ADC 118 and the voltage-dividing resistance 114 is tested and calibrated.

Although the embodiments described herein described pressure sensing to facilitate description, it is noted that the sensing device described herein and sensor 100 thereof may sense temperature, visible, infrared or ultraviolet light or intensity, or humidity, among other conditions/metrics.

Figure 7:
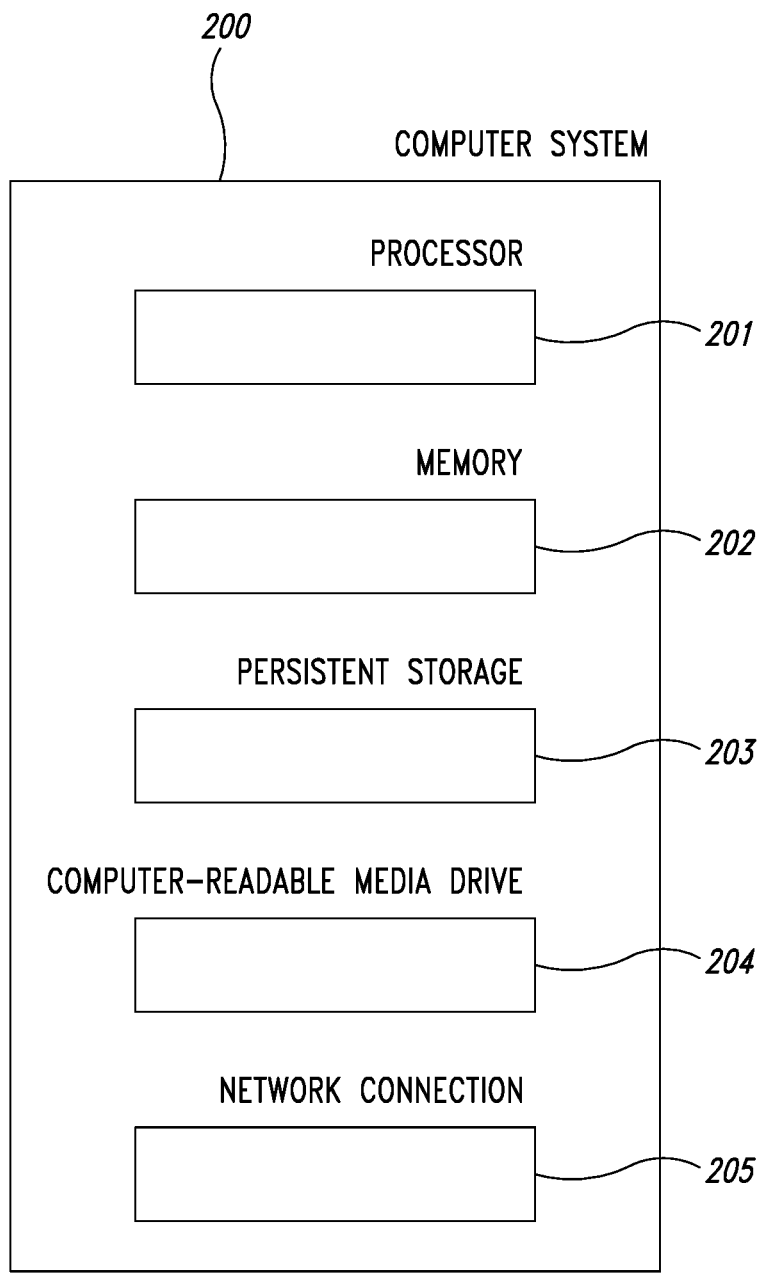
FIG. 7 is a block diagram showing some of the components typically incorporated in at least some of the computer systems and other devices on which the facility operates.

FIG. 7 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 201 for executing computer programs; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sensing device, comprising:
 a sensor configured to sense a condition and adjust a variable resistance based on the sensed condition;
 a voltage-dividing resistance serially coupled to the variable resistance via a tap node;
 an analog-to-digital converter having:
  an input coupled to the tap node and configured to receive an input voltage representative of the variable resistance;
  a reference voltage input configured to receive a reference voltage; and
  an output configured to provide an output voltage; and
 a controller having an input coupled to the output of the analog-to-digital converter and configured to receive the output voltage, the voltage-dividing resistance and the reference voltage being set such that, when a catalyst of the sensor is removed, the output voltage is less than the reference voltage.

2. The sensing device of claim 1, wherein the controller is configured to:
 determine the sensed condition based on the output voltage; and
 output, over an output of the controller, data representative of the sensed condition.

3. The sensing device of claim 2, comprising:
 a transmitter, having an input coupled to the output of the controller, configured to transmit the data representative of the sensed condition.

4. The sensing device of claim 2, wherein the sensing device is calibrated to set the voltage-dividing resistance and the reference voltage by at least:
 setting the voltage-dividing resistance to a first resistance and the reference voltage to a first voltage;
 detecting the output voltage of the analog-to-digital converter;
 setting the reference voltage to a second voltage based on the output voltage;
 determining a second resistance of the voltage-dividing resistance that causes the output voltage to be less than the reference voltage; and
 setting the voltage-dividing resistance to the second resistance.

5. The sensing device of claim 4, wherein the sensing device is calibrated to set the voltage-dividing resistance and the reference voltage by at least:
 setting the voltage-dividing resistance to the first resistance and the reference voltage to the first voltage when the catalyst of the sensor is removed; and
 setting the reference voltage to the second voltage that is less than the output voltage.

6. The sensing device of claim 4, wherein the sensing device is calibrated to set the voltage-dividing resistance and the reference voltage by at least:
 determining the second resistance by performing a binary search between a lower limit corresponding to a minimum available resistance of the voltage-dividing resistance and a higher limit corresponding to a maximum available resistance of the voltage-dividing resistance.

7. The sensing device of claim 6, wherein the sensing device is calibrated to set the voltage-dividing resistance and the reference voltage by at least:
 determining a mid-value between the lower and upper limits;
 setting the voltage-dividing resistance to the mid-value; and
 testing whether the output voltage of the analog-to-digital converter is less than the reference voltage.

8. The sensing device of claim 7, the sensing device is calibrated to set the voltage-dividing resistance and the reference voltage by at least:
 on a condition that the output voltage of the analog-to-digital converter is not less than the reference voltage, setting the lower limit to a value corresponding to the mid-value and reiterating the binary search.

9. The sensing device of claim 7, the sensing device is calibrated to set the voltage-dividing resistance and the reference voltage by at least:
 on a condition that the output voltage of the analog-to-digital converter is less than the reference voltage, setting the upper limit to a value corresponding to the mid-value and reiterating the binary search.

10. A system, comprising:
 the sensing device of claim 1; and a calibration device coupled to the sensing device and configured to calibrate the sensing device by setting the voltage-dividing resistance and the reference voltage.

11. The system of claim 10, wherein the calibration device is decoupled from the sensing device after calibrating the sensing device.

12. A calibration device, comprising:
a controller coupled to a voltage-dividing resistance controllable to have a resistance in accordance with a setting and an analog-to-digital converter configured to receive a reference voltage and convert an input voltage representative of a variable resistance to an output voltage, the controller being configured to:
set the voltage-dividing resistance to a first resistance and the reference voltage to a first voltage;
detect the output voltage of the analog-to-digital converter;
set the reference voltage to a second voltage based on the output voltage;
determine a second resistance of the voltage-dividing resistance that causes the output voltage to be less than the reference voltage; and
set the voltage-dividing resistance to the second resistance.

13. The calibration device of claim 12, wherein the variable resistance is a resistance of a sensor, and wherein the controller is configured to set the voltage-dividing resistance to the first resistance and the reference voltage to the first voltage when stimuli are removed from the sensor.

14. The calibration device of claim 12, wherein the controller is configured to set the reference voltage to the second voltage that is less than the output voltage.

15. The calibration device of claim 12, wherein the controller is configured to determine the second resistance by performing a binary search between a lower limit corresponding to a minimum available resistance of the voltage-dividing resistance and a higher limit corresponding to a maximum available resistance of the voltage-dividing resistance.

16. The calibration device of claim 15, wherein the controller is configured to perform the binary search by at least:
determining a mid-value between the lower and upper limits;
setting the voltage-dividing resistance to the mid-value; and
testing whether the output voltage of the analog-to-digital converter is less than the reference voltage.

17. The calibration device of claim 16, wherein the controller is configured to perform the binary search by at least:
on a condition that the output voltage of the analog-to-digital converter is not less than the reference voltage, setting the lower limit to a value corresponding to the mid-value and reiterating the binary search.

18. The calibration device of claim 16, wherein the controller is configured to perform the binary search by at least:
on a condition that the output voltage of the analog-to-digital converter is less than the reference voltage, setting the upper limit to a value corresponding to the mid-value and reiterating the binary search.

19. A method, comprising:
setting a voltage-dividing resistance, in a voltage divider configuration with a variable resistance representative of a sensed condition, to a first resistance;
setting a reference voltage of an analog-to-digital converter, having an input coupled to a tap node of the voltage divider, to a first voltage;
detecting an output voltage of the analog-to-digital converter;
setting the reference voltage to a second voltage based on the output voltage;
determining a second resistance of the voltage-dividing resistance that causes the output voltage to be less than the reference voltage; and
setting the voltage-dividing resistance to the second resistance.

20. The method of claim 19, comprising:
setting the voltage-dividing resistance to the first resistance and the reference voltage to the first voltage when a catalyst of the sensed condition removed; and
setting the reference voltage to the second voltage that is less than the output voltage.

21. The method of claim 19, comprising:
determining the second resistance by performing a binary search between a lower limit corresponding to a minimum available resistance of the voltage-dividing resistance and a higher limit corresponding to a maximum available resistance of the voltage-dividing resistance.

22. One or more memory devices collectively having contents adapted to cause a computing device to perform a calibration method, the method comprising:
controlling a voltage-dividing resistance of a voltage divider to be set to a first resistance, the voltage divider including the voltage-dividing resistance and a variable resistance representative of a sensed condition;
controlling a reference voltage of an analog-to-digital converter, having an input coupled to a tap node of the voltage divider, to be set to a first voltage;
determining an output voltage of the analog-to-digital converter;
controlling the reference voltage to be set, based on the output voltage, to a second voltage;
determining a second resistance of the voltage-dividing resistance that causes the output voltage to be less than the reference voltage; and
controlling the voltage-dividing resistance to be set to the second resistance.

* * * * *